United States Patent
Kho et al.

(10) Patent No.: US 8,506,937 B2
(45) Date of Patent: Aug. 13, 2013

(54) ARTIFICIAL SALIVA COMPRISING HYALURONIC ACID

(75) Inventors: Hong Seop Kho, Seoul (KR); Moon Soo Park, Gangwon-do (KR)

(73) Assignee: SNU R&DB Foundation, Seoul (KR)

( * ) Notice: Subject to any disclaimer, the term of this patent is extended or adjusted under 35 U.S.C. 154(b) by 0 days.

(21) Appl. No.: 13/388,416

(22) PCT Filed: Apr. 1, 2011

(86) PCT No.: PCT/KR2011/002292
§ 371 (c)(1),
(2), (4) Date: Feb. 1, 2012

(87) PCT Pub. No.: WO2012/093753
PCT Pub. Date: Jul. 12, 2012

(65) Prior Publication Data
US 2012/0321605 A1 Dec. 20, 2012

(51) Int. Cl.
*A61Q 11/00* (2006.01)
(52) U.S. Cl.
USPC .......................................... 424/49; 424/94.61
(58) Field of Classification Search
USPC ................................................ 424/49, 94.61
See application file for complete search history.

(56) References Cited

U.S. PATENT DOCUMENTS

2007/0099827 A1 * 5/2007 Uotani et al. .................. 514/12

FOREIGN PATENT DOCUMENTS

JP 2007-291117 11/2007
WO WO 00/56344 * 9/2000

OTHER PUBLICATIONS

Park et al., "Rheological properties of hyaluronic acid and its effects on salivary enzymes and *candida*", 2010, Oral Diseases, 16, pp. 382-387.
Lee et al., "The effects of peroxidase on the enzymatic and candidacidal activities of lysozyme", 2010, Archives of Oral Biology, 55, pp. 607-612.
Written Opinion for International Patent Application No. PCT/KR2011/002292 mailed Feb. 6, 2012.
International Search Report for International Patent Application No. PCT/KR2011/002292 mailed Feb. 6, 2012.

* cited by examiner

*Primary Examiner* — Ralph Gitomer
(74) *Attorney, Agent, or Firm* — Swanson & Bratschun, LLC

(57) ABSTRACT

Provided is artificial saliva including hyaluronic acid (HA) comprising 0.4 to 0.6 mg/ml of hyaluronic acid (HA), based on 100 parts by weight of the HA, 10 to 12 parts by weight of lysozyme, and 7 to 9 parts by weight of peroxidase. The artificial saliva may be used to treat xerostomia or oral candidiasis and can be effectively used to prevent or treat complications cased by reduced secretion of saliva, since the artificial saliva is in a physiological range of human saliva and shows adequate antimicrobial activities.

7 Claims, 3 Drawing Sheets

ARTIFICIAL SALIVA COMPRISING HYALURONIC ACID

RELATED APPLICATIONS

This application is a 35 U.S.C. §371 national phase application of PCT/KR2011/002292, filed on Apr. 1, 2011, entitled "ARTIFICIAL SALIVA COMPRISING HYALULONIC ACID", which application claims the benefit of Korean Application No. 10-2011-0000800, filed Jan. 5, 2011, which is incorporated herein by reference in its entirety.

TECHNICAL FIELD

The present invention relates to artificial saliva including hyaluronic acid.

BACKGROUND ART

Hyaluronic acid (HA) is a glycosaminoglycan consisting of alternating D-glucuronic acid and N-acetyl-D-glucosamine units. The D-glucuronic acid and the N-acetyl-D-glucosamine are linked via a β (1→3) bond, while the N-acetyl-D-glucosamine and the D-glucuronic acid are linked via a β (1→4) bond. HA is abundant in the vitreous humor of the eye, the synovial fluid of articular joints, and the extracellular matrix. Due to its innate biocompatibility and unique physical properties, HA has been used for delivery of drugs, preparation of a biocompatible material, artificial tears for xerophthalmic patients, and a substances for relieving symptoms of osteoarthritis.

The presence of HA in human saliva has been reported and HA in saliva may contribute to the lubricating and healing properties of saliva, and assisting in protecting the oral mucosa. HA has also been reported to display anti-*Candida* activity. Due to its viscoelastic properties and non-immunogenicity, it is known that HA may be considered as a candidate for substitution of xerostomic patients saliva, and shows similar physical properties to human saliva at a certain concentration.

The relation between the reduction of HA in the saliva and the occurrence of xerostomia is known, which proves that HA serves to protect and lubricate the oral mucosa. In addition, the wound healing activity and the potential anti-*Candida* activity of HA may provide an additional advantage to patients suffering from dry mouth who are vulnerable to oral mucosal injuries and candidiasis.

There have been attempts to strengthen and recover an antimicrobial ability of saliva using commercially available oral hygiene products. Antimicrobial proteins most widely used in the oral hygiene products include lysozyme and lactoperoxidase. The antimicrobial proteins were introduced into a saliva substitute to recover the antimicrobial ability of the saliva of a patient suffering from dry mouth, who was vulnerable to candidiasis. The antifungal activities of the lysozyme and the antifungal activities of the peroxidase system are known. It is known that lysozyme and peroxidase were used together to increase the *Candida*-killing activity. It has not been confirmed that the in vitro experimental results were applied to an in vivo environment in the same manner, but the antimicrobial supplements may reduce development of candidiasis in xerostomic patients.

The oral cavity provides an environment where saliva substitutes and saliva molecules can be present at the same time. Therefore, the HA molecules of the saliva substitutes will also interact with the antimicrobial molecules of human saliva. The presence of an HA-lysozyme complex (Van Damme et al. Binding of Hyaluronan to Lysozyme at Various PHSA, Biochemistry International, 1991 July 24(4), 605-13; Van Damme et al. Binding Properties of Glycosaminoglycans to Lysozyme-Effect of Salt and Molecular Weight, Archives of Biochemistry and Biopbysics, 1994 April, 310(1), 16-24; Moss et al. Dependence of Salt Concentration on Glycosaminoglycan-Lysozyme Interactions in Cartilage, Archives of Biochemistry and Biophysics, 1997 Dec. 1, 348(1), 49-55) and the HA-peroxidase complex (Green et al. Depolymerization of Synovial Fluid Hyaluronic Acid (HA) by the Complete Myeloperoxidase (MPO) System May Involve the Formation of a HA-MPO Ionic Complex, The Journal of Rheumatology, 1990, 17:12, 1670-5) was proposed in the prior-art literatures.

However, it is not known how and what HA affects the anti-*Candida* activities of lysozyme and peroxidase.

DISCLOSURE OF INVENTION

Technical Problem

Therefore, an object of the present invention is to provide artificial saliva including hyaluronic acid (HA).

Another object of the present invention is to provide a concentration of HA, suitable as artificial saliva, and concentrations of lysozyme and peroxidase which are antimicrobial additives.

Solution to Problem

The present invention provides artificial saliva including 0.4 to 0.6 mg/ml of HA, characterized in that the artificial saliva includes 10 to 12 parts by weight of lysozyme, and 7 to 9 parts by weight of peroxidase, based on 100 parts by weight of the HA.

According to one embodiment of the present invention, the lysozyme in the artificial saliva may be present in a concentration of 50 to 60 µg/ml based on the total amount of the artificial saliva, or the peroxidase in the artificial saliva may be present in a concentration of 36 to 43 µg/ml based on the total amount of the artificial saliva.

According to another embodiment of the present invention, a molecular weight of the HA may be in a range of 100 kDa to 10,000 kDa, but the present invention is not particularly limited thereto.

The artificial saliva according to the present invention may be used to treat xerostomia or oral candidiasis, and may also be used to prevent or treat complications caused by reduced secretion of saliva. Therefore, the present invention provides artificial saliva for treatment of xerostomia or oral candidiasis, or artificial saliva for prevention or treatment of complications caused by reduced secretion of saliva, wherein the artificial saliva includes HA.

Advantageous Effects of Invention

The artificial saliva according to the present invention can be used to treat xerostomia or oral candidiasis and effectively used to prevent or treat complications cased by reduced secretion of saliva since the artificial saliva is in a physiological range of human saliva and shows adequate antimicrobial activities.

BEST MODE FOR CARRYING OUT THE INVENTION

Figure 1:
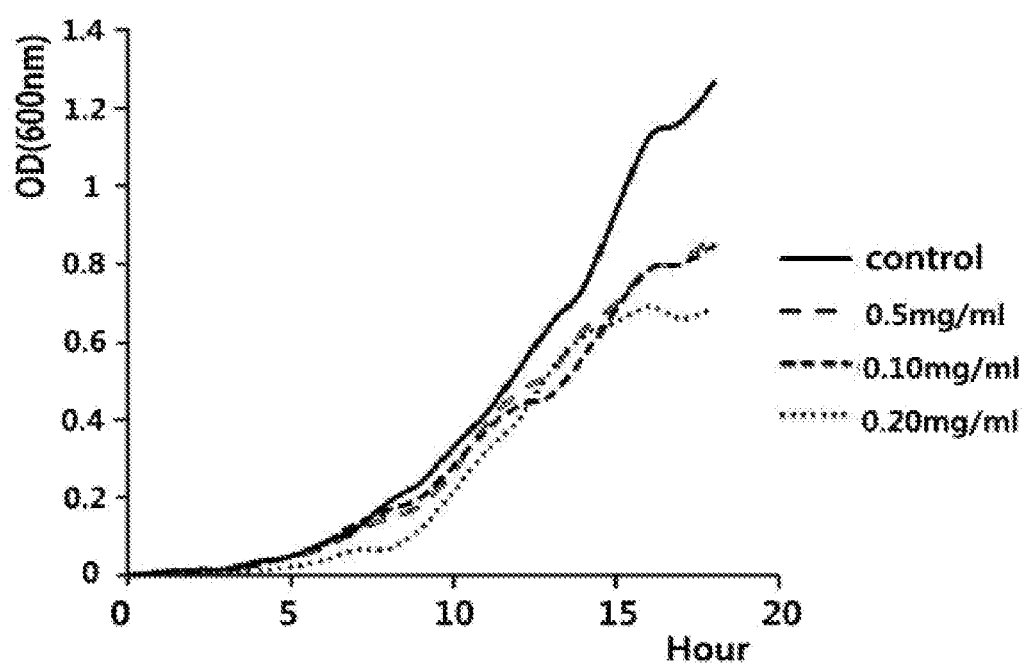
FIG. 1 is a graph illustrating inhibitory effects of HA on growth of *C. albicans* ATCC 10231.

Hereinafter, the present invention will be described with reference to examples and comparative examples in detail. However, the present invention is not limited to these examples.

The present invention provides artificial saliva including 0.4 to 0.6 mg/ml hyaluronic acid (HA), characterized in that the artificial saliva includes 10 to 12 parts by weight of lysozyme; and 7 to 9 parts by weight of peroxidase, based on 100 parts by weight of the HA.

In the present invention, since the HA conceptually includes both HA and salts thereof, the term "HA" used in the present invention means hyaluronic acid, hyaluronate, or a mixture of hyaluronic acid and hyaluronate. The hyaluronate includes both an inorganic salt such as sodium hyaluronate, potassium hyaluronate, calcium hyaluronate, magnesium hyaluronate, zinc hyaluronate or cobalt hyaluronate and an organic salt such as hyaluronate tetrabutylammonium. When necessary, they may be used in a combination thereof.

Lysozyme is an enzyme that hydrolyzes a β-1,4-glycosidic bond between N-acetylmuramic acid (NAM) and N-acetylglucosamine (NAG) in polysaccharides present in the bacterial cell wall. In general, the lysozyme is included in egg whites, animal tissue, nasal mucosa, sputum, gastric juice, tears, etc., and has germicidal and antimicrobial activities.

Peroxidase means an enzyme that catalyzes an oxidation reaction so that monoamines, polyamines, monophenols, polyphenols, leuco pigments, ascorbic acid, cytochrome C, HI and so on can be represented by the following scheme in the presence of $H_2O_2$ (or $CH_3OOH$): $H_2O_2 + AH_2 \rightarrow 2H_2O + A$.

HA is most suitable as a saliva substitute in aspects of the rheology when the HA is prepared in a concentration of 0.5 mg/ml in a buffer having similar compositions to the saliva (a simulated salivary buffer). Also, as the antimicrobial additives, the lysozyme may be added at an amount of 10 to 12 parts by weight, based on 100 parts by weight of the HA, and the peroxidase may be added at an amount of 7 to 9 parts by weight, based on 100 parts by weight of the HA. In this case, the artificial saliva is in a physiological range of human saliva and shows adequate antimicrobial activities.

In the present invention, the term "part by weight" means a weight ratio.

When the lysozyme is present as the antimicrobial additive at an amount of less than 10 parts by weight based on 100 parts by weight of the HA, or the peroxidase is present at an amount of less than 7 parts by weight based on 100 parts by weight of the HA, the antifungal activities of the artificial saliva may be insufficient.

According to one embodiment of the present invention, the lysozyme in the artificial saliva may be present in a concentration of 50 to 60 μg/ml based on the total amount of the artificial saliva, or the peroxidase in the artificial saliva may be present in a concentration of 36 to 43 μg/ml based on the total amount of the artificial saliva.

According to another embodiment of the present invention, a molecular weight of the HA may be in a range of 100 kDa to 10,000 kDa, but the present invention is not particularly limited thereto.

The artificial saliva according to the present invention may be used to treat xerostomia or oral candidiasis, and may be used to prevent or treat complications cased by reduced secretion of saliva. Therefore, the present invention provides artificial saliva for treatment of xerostomia or oral candidiasis, as well as artificial saliva for prevention or treatment of complications caused by reduced secretion of saliva, wherein the artificial saliva includes HA.

MODE FOR THE INVENTION

Hereinafter, exemplary embodiments of the present invention will be described in further detail for the purpose of better understanding. However, the description proposed herein is merely a preferable example for the purpose of illustration only, not intended to limit the scope of the invention, so it should be understood that other equivalents and modifications could be made thereto without departing from the scope of the invention.

The following Preparative Examples are designed to provide Preparative Examples applied commonly to Examples according to the present invention.

Preparative Example 1

HA Solution

HA (1,630 kDa, Sigma-Aldrich, St Louis, Mo., USA) was dissolved in a buffer having similar composition to saliva (a stimulated salivary buffer, including SSB, 0.021 M $Na_2HPO_4/NaH_2PO_4$, pH 7.0, 36 mM NaCl and 0.96 mM $CaCl_2$) or RPMI 1640 media having three different concentrations (0.5, 1.0 and 2.0 mg/ml).

Preparative Example 2

Lysozyme and Peroxidase

Hen egg-white lysozyme (HEWL) and bovine lactoperoxidase (bLPO) (Sigma-Aldrich, St Louis, Mo., USA), which were used as the lysozyme and peroxidase of the present invention respectively, were dissolved in SSB. For the analysis, the HEWL was used in a concentration of 30.0 μg/ml, or the bLPO was used in a concentration of 25.0 μg/ml.

Example 1

Fungal Growth Inhibiting Activity of HA

*Candida albicans* ATCC 10231, 18804 and 11006 were used in this experiment. One colony of each of *C. albicans* grown in a Sabouraud dextrose agar (SDA) was inoculated in a Sabouraud dextrose medium, and incubated at 37° C. for 18 hours while stiffing. Cells were harvested, washed, and re-suspended in an RPMI 1640 medium at a concentration of $1 \times 10^5$ cells/ml. In order to measure the fungal growth inhibiting activity of HA, HA was dissolved in 100 ml of RPMI 1640 medium containing *C. albicans* at various concentrations (0.5, 0.1 and 2.0 mg/ml), and incubated at 37° C. while stirring. A proliferative phase was determined by measuring an optical density of a culture medium at 600 nm at a time interval of 1 hour, and the optical density of the culture medium was compared to that of an HA-free culture medium. This experiment was repeated four times.

HA showed an inhibitory effect on the growth of *C. albicans*, and the inhibitory effect was in proportion to the concentration of HA used in this experiment. The HA had the highest inhibitory effect at the *C. albicans* ATCC 11006 cell line, and the lowest inhibitory effect at the *C. albicans* ATCC 18804 cell line (see FIGS. 1, 2 and 3).

Example 2

Candida-Killing Activity of HA

One colony of each of *C. albicans* ATCC 10231, 18804 and 11006 was inoculated in 10 ml of an RPMI 1640 medium, and incubated at 37° C. for 18 hours while stirring. Cells were harvested, washed, and re-suspended in SSB at a concentration of $1 \times 10^5$ cells/ml. In order to measure the *Candida*-killing activity of HA, 20 µl of a cell suspension was added at various concentrations to 40 µl of HA (final concentrations: 0.5, 1.0 and 2.0 mg/ml). Samples were incubated at 37° C. for 1.5 hours, and mixed every 15 minutes. The final culture samples were diluted 10 times, and 50 µl (167 cells) of the diluted culture samples were plated on an SDA plate in triplicate and incubated overnight at 37° C. The *Candida*-killing activity was measured by comparing the number of colonies on an experimental plate to the number of colonies on an HA-free control plate. Also, the loss in cell viability (1−colonies of experimental plate/colonies of control plate×100) was calculated. This experiment was repeated six times.

HA (final concentrations: 0.5, 1.0 and 2.0 mg/ml) showed no measurable *Candida*-killing activity and showed no significant difference in number of colonies on the experimental plate at all the cell lines, compared to that of the control (free of HA).

while stirring. 40 µl of the cell suspension was mixed with 20 µl of HEWL (final concentration: 30 µg/ml) or 20 µl of peroxidase (final concentration: 25 µg/ml bLPO, 1 mM KSCN and 100 µM $H_2O_2$), and then incubated at 37° C. for 1 hour while stirring. At the end of incubation, the samples were diluted 10 times, and 50 µl (167 cells) of the diluted samples were plated on an SDA plate in triplicate and incubated overnight at 37° C. The *Candida*-killing activity and the loss in cell viability were calculated. This experiment was repeated eight times.

HA showed an inhibitory effect on the *Candida*-killing activity of the lysozyme and peroxidase systems, and the inhibitory effect was in proportion to the concentration of HA. Inhibition levels were different according to the *C. albicans* cell lines, but the *Candida*-killing activities of the lysozyme and peroxidase systems used in this experiment were completely inhibited at 1.0 to 2.0 mg/ml of HA (see Tables 1 and 2).

TABLE 1

| *C. albicans* cell lines | N = 8 | Control (Group I) | HEWL (Group II) | HEWL + 0.5 mg/ml HA (Group III) | HEWL + 1.0 mg/ml HA (Group IV) | HEWL + 2.0 mg/ml HA (Group V) |
|---|---|---|---|---|---|---|
| ATCC 10231 | CFU | 154.5 ± 26.5 | 106.8 ± 15.6 | 126.8 ± 27.5 | 120.4 ± 39.7 | 144.3 ± 24.6 |
|  | % killing | — | 28.7 ± 17.3 | 15.9 ± 22.3 | 20.5 ± 25.3 | 5.3 ± 15.8 |
| ATCC 18804 | CFU | 143.9 ± 18.3 | 104.8 ± 12.8 | 138.4 ± 24.6 | 136.6 ± 27.6 | 155.1 ± 18.8 |
|  | % killing | — | 26.9 ± 6.7 | 3.3 ± 16.2 | 3.8 ± 23.8 | −8.9 ± 16.3 |
| ATCC 11006 | CFU | 157.9 ± 18.0 | 105.8 ± 24.9 | 150.6 ± 21.8 | 155.1 ± 19.0 | 161.3 ± 12.7 |
|  | % killing | — | 32.6 ± 16.2 | 4.6 ±9.5 | 1.4 ± 10.7 | −2.8 ± 8.8 |

The effects of HA on the *Candida*-killing activity of lysozyme (when HA was incubated with *Candida* cells and then treated with the lysozyme)

HEWL: hen egg-white lysozyme; and CFU: colony forming unit

TABLE 2

| *C. albicans* cell lines | N = 8 | Control (Group I) | HEWL (Group II) | HEWL + 0.5 mg/ml HA (Group III) | HEWL + 1.0 mg/ml HA (Group IV) | HEWL + 2.0 mg/ml HA (Group V) |
|---|---|---|---|---|---|---|
| ATCC 10231 | CFU | 154.5 ± 26.5 | 106.8 ± 15.6 | 126.8 ± 27.5 | 120.4 ± 39.7 | 144.3 ± 24.6 |
|  | % killing | — | 28.7 ± 17.3 | 15.9 ± 22.3 | 20.5 ± 25.3 | 5.3 ± 15.8 |
| ATCC 18804 | CFU | 143.9 ± 18.3 | 104.8 ± 12.8 | 138.4 ± 24.6 | 136.6 ± 27.6 | 155.1 ± 18.8 |
|  | % killing | — | 26.9 ± 6.7 | 3.3 ± 16.2 | 3.8 ± 23.8 | −8.9 ± 16.3 |
| ATCC 18804 | CFU | 157.9 ± 18.0 | 105.8 ± 24.9 | 150.6 ± 21.8 | 155.1 ± 19.0 | 161.3 ± 12.7 |
|  | % killing | — | 32.6 ± 16.2 | 4.6 ± 9.5 | 1.4 ± 10.7 | −2.8 ± 8.8 |

The effects of HA on the *Candida*-killing activity of peroxidase (when HA was incubated with *Candida* cells and then treated with the peroxidase)

bLPO: bovine lactoperoxidase; and CFU: colony forming unit

Example 3

Effects of HA on *Candida*-Killing Activity of Lysozyme and Peroxidase

When HA was Incubated with *Candida* Cells and Then Treated with an Antimicrobial Enzyme A cell suspension of *C. albicans* incubated as described above was applied to SSB at a concentration of $1 \times 10^5$ cells/ml, and 20 µl of the cell suspension was then added to an equivalent amount of HA (final concentrations: 0.5, 1.0 and 2.0 mg/ml). Samples were incubated at 37° C. for 1 hour

Example 4

Effects of HA on *Candida*-Killing Activity of Lysozyme and Peroxidase

When HA was Incubated with an Antimicrobial Enzyme and Then Treated with *Candida* Cells 20 µl of an HA solution (final concentrations: 0.5, 1.0 and 2.0 mg/ml) was added to 20 µl of HEWL (final concentration:

30 μg/ml) or 20 μl of peroxidase (final concentration: 25 μg/ml bLPO, 1 mM KSCN and 100 μM $H_2O_2$) and then incubated at 37° C. for 1 hour while stirring. The resulting mixture was added to 20 μl of a cell suspension and incubated at 37° C. for 1 hour while stirring. At the end of incubation, the samples were diluted 10 times, and 50 μl (167 cells) of the diluted samples were plated on an SDA plate in triplicate, and incubated overnight at 37° C. The *Candida*-killing activity and the loss in cell viability were calculated. This experiment was repeated eight times.

When HA was first incubated with the antimicrobial enzyme, the HA also showed similar inhibitory effects on the *Candida*-killing activity of the lysozyme and peroxidase systems. The *Candida*-killing activities of the lysozyme and peroxidase systems used in this experiment were deactivated at 1.0 to 2.0 mg/ml of HA (see Tables 3 and 4).

TABLE 3

| *C. albicans* cell lines | N = 8 | Control (Group I) | HEWL (Group II) | HEWL + 0.5 mg/ml HA (Group III) | HEWL + 1.0 mg/ml HA (Group IV) | HEWL + 2.0 mg/ml HA (Group V) |
|---|---|---|---|---|---|---|
| ATCC 10231 | CFU | 160.9 ± 12.1 | 118.1 ± 16.5 | 152.4 ± 25.9 | 161.8 ± 19.4 | 165.9 ± 24.5 |
|  | % killing | — | 26.6 ± 8.9 | 5.3 ± 14.2 | −0.5 ± 8.9 | −3.1 ± 13.1 |
| ATCC 18804 | CFU | 143.0 ± 22.7 | 105.1 ± 26.9 | 136.2 ± 17.6 | 143.5 ± 29.4 | 142.2 ± 22.5 |
|  | % killing | — | 26.9 ± 11.8 | 3.4 ± 14.6 | −0.5 ± 12.4 | 0.2 ± 9.6 |
| ATCC 11006 | CFU | 152.2 ± 20.7 | 118.3 ± 10.6 | 148.8 ± 18.9 | 153.7 ± 19.1 | 151.9 ± 29.1 |
|  | % killing | — | 21.5 ± 8.9 | 1.5 ± 11.3 | −1.7 ± 11.6 | −0.9 ± 19.7 |

The effects of HA on the *Candida*-killing activity of lysozyme (when HA was incubated with the lysozyme and then treated with *Candida* cells)

HEWL: hen egg-white lysozyme; and CFU: colony forming unit

TABLE 4

| *C. albicans* cell lines | N = 8 | Control (Group I) | bLPO System (Group II) | bLPO System + 0.5 mg/ml HA (Group III) | bLPO System + 1.0 mg/ml HA (Group IV) | bLPO System + 2.0 mg/ml HA (Group V) |
|---|---|---|---|---|---|---|
| ATCC 10231 | CFU | 155.6 ± 22.9 | 118.3 ± 19.6 | 133.0 ± 18.5 | 144.9 ± 24.7 | 160.4 ± 16.6 |
|  | % killing | — | 23.2 ± 13.3 | 13.0 ± 17.6 | 6.1 ± 16.0 | −4.2 ± 12.8 |
| ATCC 18804 | CFU | 159.1 ± 5.7 | 112.6 ± 8.5 | 139.8 ± 15.2 | 146.6 ± 13.6 | 144.8 ± 11.2 |
|  | % killing | — | 29.2 ± 5.0 | 12.1 ± 9.8 | 7.8 ± 8.6 | 8.9 ± 7.6 |
| ATCC 11006 | CFU | 154.0 ± 13.6 | 101.3 ± 18.6 | 132.1 ± 20.5 | 134.5 ± 17.4 | 143.6 ± 12.9 |
|  | % killing | — | 34.0 ± 11.9 | 14.1 ± 12.1 | 12.6 ± 8.4 | 6.4 ± 9.1 |

The effects of HA on the *Candida*-killing activity of peroxidase (when HA was incubated with the peroxidase and then treated with *Candida* cells)

bLPO: bovine lactoperoxidase; and CFU: colony forming unit 0.5 mg/ml of HA inhibited 79.8±7.7% of the *Candida*-killing activity of the lysozyme and 58.8±4.7% of the *Candida*-killing activity of the peroxidase. Therefore, the lysozyme and the peroxidase may be added at concentrations of approximately 54.0 μg/ml (50 to 60 μg/ml) and approximately 39.7 μg/ml (36 to 43 μg/ml), respectively, to improve the antifungal activities.

While the invention has been shown and described with reference to certain exemplary embodiments thereof, it will be understood by those skilled in the art that various changes in form and details may be made therein without departing from the scope of the invention as defined by the appended claims.

The invention claimed is:

1. Artificial saliva comprising 0.4 to 0.6 mg/ml of hyaluronic acid (HA), comprising; based on 100 parts by weight of the HA, 10 to 12 parts by weight of lysozyme, and 7 to 9 parts by weight of peroxidase.

2. The artificial saliva according to claim 1, wherein the lysozyme in the artificial saliva is present in a concentration of 50 to 60 μg/ml based on the total amount of the artificial saliva.

3. The artificial saliva according to claim 1, wherein the peroxidase in the artificial saliva is present in a concentration of 36 to 43 μg/ml based on the total amount of the artificial saliva.

4. The artificial saliva according to claim 1, wherein the HA is HA itself, hyaluronate, or a mixture of HA and hyaluronate, and the hyaluronate is an inorganic salt selected from the group consisting of sodium hyaluronate, potassium hyaluronate, calcium hyaluronate, magnesium hyaluronate, zinc hyaluronate and cobalt hyaluronate, or organic salts such as hyaluronate tetrabutylammonium.

5. The artificial saliva according to claim 1, wherein the HA has a molecular weight of 100 kDa to 10,000 kDa.

6. The artificial saliva according to claim 1, wherein the artificial saliva is used to treat xerostomia or oral candidiasis.

7. The artificial saliva according to claim 1, wherein the artificial saliva is used to prevent or treat complications cased by reduced secretion of saliva.

* * * * *

UNITED STATES PATENT AND TRADEMARK OFFICE
CERTIFICATE OF CORRECTION

PATENT NO. : 8,506,937 B2
APPLICATION NO. : 13/388416
DATED : August 13, 2013
INVENTOR(S) : Hong Seop Kho et al.

It is certified that error appears in the above-identified patent and that said Letters Patent is hereby corrected as shown below:

In the Drawings

Figure 1, delete "0.10mg/ml and 0.20mg/ml" and add "1.0mg/ml and 2.0mg/ml" respectively.

Figure 2:
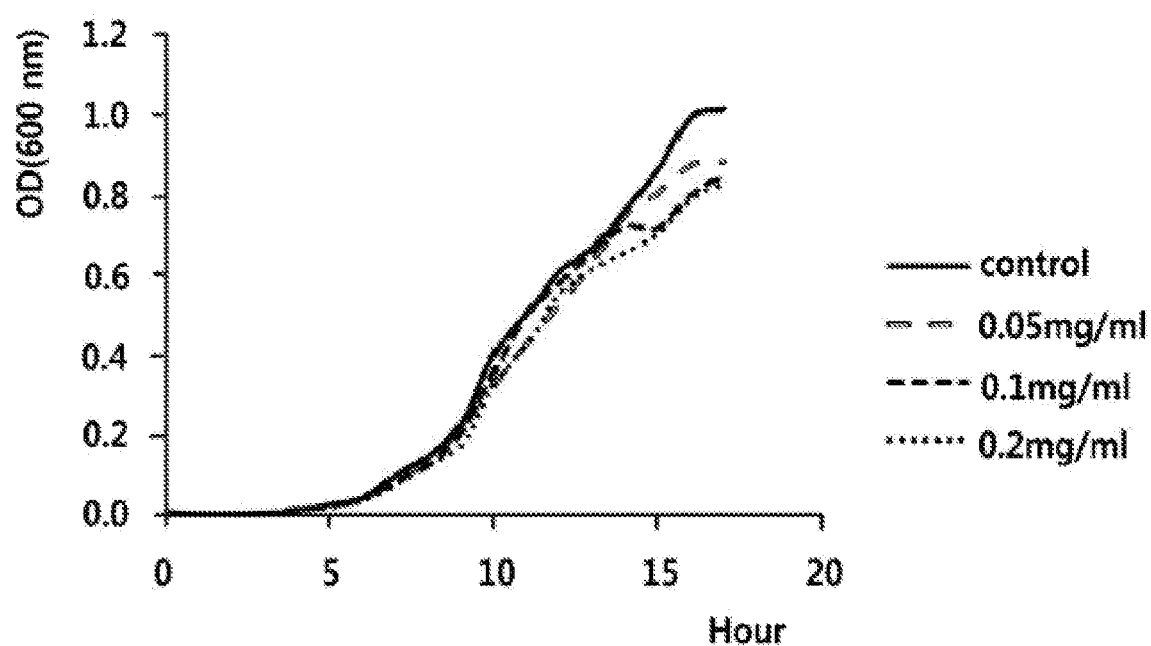
FIG. 2 is a graph illustrating inhibitory effects of HA on growth of *C. albicans* ATCC18804.

Figure 2, delete "0.05mg/ml, 0.1mg/ml, and 0.2mg/ml" and add "0.5mg/ml, 1.0mg/ml, and 2.0mg/ml" respectively.

Figure 3:
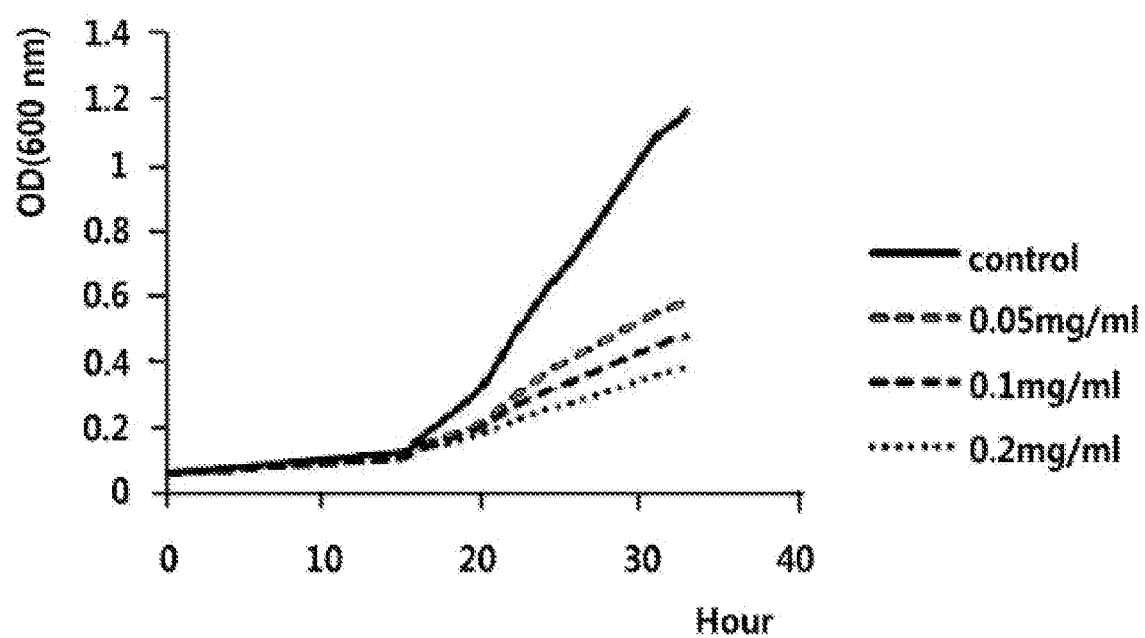
FIG. 3 is a graph illustrating inhibitory effects of HA on growth of *C. albicans* ATCC11006.

Figure 3, delete "0.05mg/ml, 0.1mg/ml, and 0.2mg/ml" and add "0.5mg/ml, 1.0mg/ml, and 2.0mg/ml" respectively.

In the Specifications

Column 4, line 56, delete "(0.5, 0.1 and 2.0 mg/ml)" and add "(0.5, 1.0 and 2.0 mg/ml)" therefor.

Signed and Sealed this
Fourteenth Day of January, 2014

Michelle K. Lee
*Deputy Director of the United States Patent and Trademark Office*